United States Patent [19]

Rosenman et al.

[11] Patent Number: 5,423,857
[45] Date of Patent: Jun. 13, 1995

[54] THREE PIECE SURGICAL STAPLE

[75] Inventors: Daniel C. Rosenman, Hazlet; Shawn T. Huxel, Lakehurst; Brian H. Luscombe, Warren, all of N.J.

[73] Assignee: Ethicon, Inc., Somerville, N.J.

[21] Appl. No.: 146,755

[22] Filed: Nov. 2, 1993

[51] Int. Cl.6 .......................................... A61B 17/04
[52] U.S. Cl. ................................. 606/219; 606/104; 606/151; 411/457
[58] Field of Search ............... 606/215, 216, 219, 220, 606/151, 104; 411/457

[56] References Cited

U.S. PATENT DOCUMENTS

| 3,068,869 | 12/1962 | Shelden et al. | 606/216 |
|-----------|---------|----------------|---------|
| 4,317,451 | 3/1982  | Cerwin et al.  | 606/219 |
| 4,428,376 | 1/1984  | Mericle        | 606/219 |
| 4,531,522 | 7/1985  | Bedi et al.    | 606/220 |
| 4,610,250 | 9/1986  | Green          | 606/220 |
| 4,719,917 | 1/1988  | Barrows et al. | 606/220 |
| 4,741,336 | 5/1988  | Failla et al.  | 606/220 |
| 4,887,601 | 12/1989 | Richards       | 606/219 |

FOREIGN PATENT DOCUMENTS 0122046  9/1984  European Pat. Off. .

Primary Examiner—Gary Jackson
Attorney, Agent, or Firm—Emil Richard Skula

[57] ABSTRACT

A surgical staple for use in surgical procedures. The surgical staple has a crown having a hollow frame. The frame has a top slot in communication with the interior of the crown frame. At least two legs are pivotally mounted in the frame such that when the staple is inserted into tissue and the legs are rotated inwardly, the staple secures tissue and the legs are locked in a fixed position. In an alternate embodiment, at least one leg is pivotally mounted to the frame and at least one leg is fixedly mounted to the frame.

33 Claims, 9 Drawing Sheets

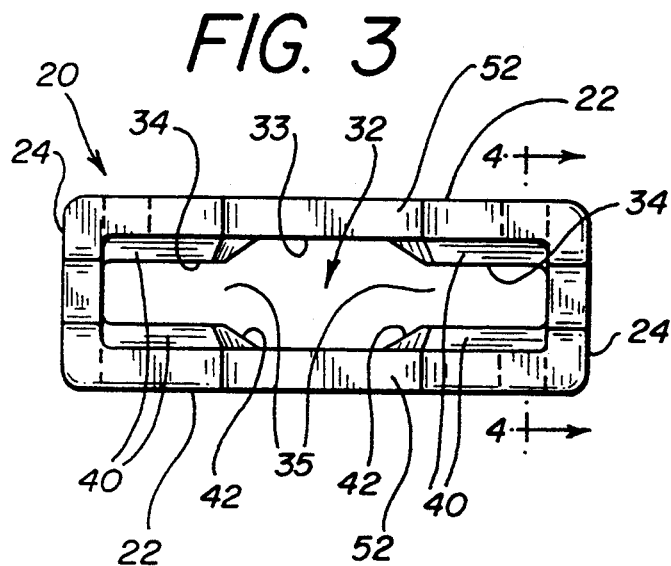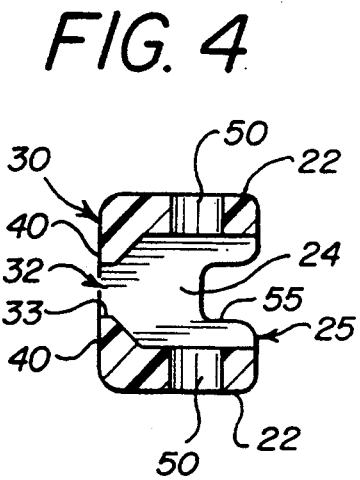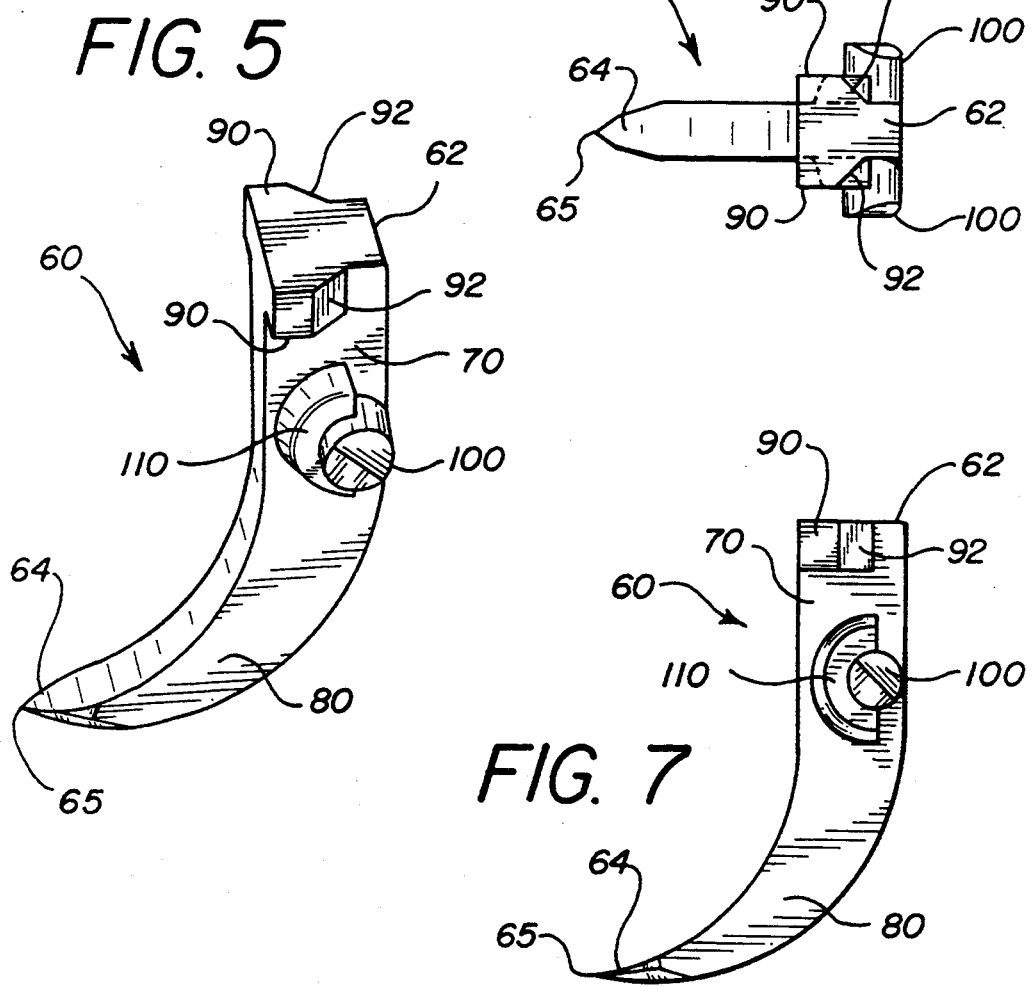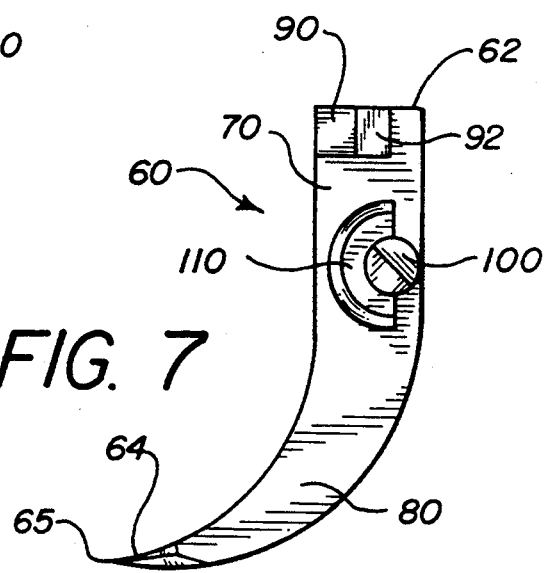

THREE PIECE SURGICAL STAPLE

TECHNICAL FIELD

The field of art to which this invention relates is surgical devices, more particularly, surgical staples.

BACKGROUND ART

Surgical staples are well known in the surgical arts. These staples have been widely used by physicians to close incisions. Surgical staples have proven to be a useful alternative available to the physician in lieu of conventional sutures.

Surgical staples have also been used in various surgical procedures. For example, when performing a surgical procedure to repair an inguinal hernia, one common technique is to affix a biocompatible surgical mesh over the site of the inguinal hernia. This is typically done by stapling the surgical mesh to the tissue and muscle surrounding the site of the hernia. The staples used in this procedure are, typically, conventional metal staples made from stainless steel, titanium, tantalum, or the like. There are several disadvantages associated with the use of metal staples in such an operation. One obvious disadvantage is that the metal staple remains inside of the patient indefinitely. In addition, it is not uncommon for a nerve to be entrapped and compressed by a metal staple. It is believed that this may cause residual pain in the patient. In order to alleviate such pain, a subsequent operation may be required to remove and/or replace the staples.

The use of absorbable staples may help to overcome this problem and eliminate the need for additional surgery since the absorbable staple would absorb over time, thereby relieving any pressure upon a compressed nerve. Although absorbable staples are known in this art, such staples typically require access to both sides of a tissue site since they typically consist of an upper section having a crown and legs and a lower receiver. The lower receiver engages and locks the legs of the staple. Therefore, the absorbable staples known in the art are typically not usable in surgical procedures such as repair of an inguinal hernia where there is only access to one side of the tissue.

Therefore, there is a need in this art for an absorbable staple which does not require a second separate piece to lock the staple into place in tissue and which can be applied and secured from one side of the tissue in an endoscopic or open surgical procedure.

DISCLOSURE OF THE INVENTION

Accordingly, it is an object of the present invention to provide a novel surgical staple which can be applied to tissue from a single side in a conventional manner.

It is a further object of the present invention to provide an absorbable surgical staple which can be applied and locked in place without the need for a separate receiver.

It is yet a further object of the present invention to provide an absorbable surgical staple which can be used in a multiple feed stapling apparatus.

It is still yet a further object of the present invention to provide an absorbable surgical staple which can be used in an endoscopic procedure.

Still yet a further object of the present invention is to provide a device for applying the staples of the present invention.

Accordingly, a novel surgical staple is disclosed. The surgical staple comprises an upper crown comprising a frame having a cavity therein. The crown has a slot in the top of the frame in communication with the cavity. A pair of legs is pivotally mounted in the crown. Each leg has a distal pointed end for piercing tissue and a proximal end. It is particularly preferred that the legs be curved. Locking flaps for locking the legs in a fixed position relative to the frame are mounted to proximal ends of each leg. A slot and flaps for engaging the locking flaps of the legs are mounted in the crown. The proximal end of each leg is movable through at least part of the slot. It is particularly preferred that the staple be made from an absorbable material. Optionally, more than one leg may be mounted in the frame. Also, an optional fixed leg may extend from the frame.

Yet another aspect of the preset invention is a method of performing a surgical procedure using the above-described surgical staple.

Yet another aspect of the present invention is a device for applying the staples of the present invention. The device consists of a tubular frame having a distal end and a proximal end. A handle is mounted to the proximal end of the tubular member while a staple holding member is mounted to its distal end. An actuation rod is slidably mounted in the tubular member. The distal end of the rod is mounted to an actuating member having a shape which tapers from a maximum distal dimension to a minor proximal dimension, preferably a conical or triangular shape. The proximal end of the rod is mounted to an actuation means such as a lever pivotally mounted to the handle. Proximal motion of the actuation rod causes the actuating member to engage and lock the legs of a staple of the present invention.

Other features and advantages of the invention will become more apparent from the following description and accompanying drawings.

BRIEF DESCRIPTION OF THE DRAWINGS

FIG. 3 is a bottom view of the crown of the surgical staple;

FIG. 4 is a side cross-sectional view of the crown of the surgical staple as taken along View Line 4—4 of FIG. 3;

FIG. 5 is a perspective view of a leg of the surgical staple;

FIG. 6 is a top view of the leg of the surgical staple of FIG. 5;

FIG. 7 is a side view of the leg of the surgical staple of FIG. 5;

BEST MODE FOR CARRYING OUT THE INVENTION

Figure 1:
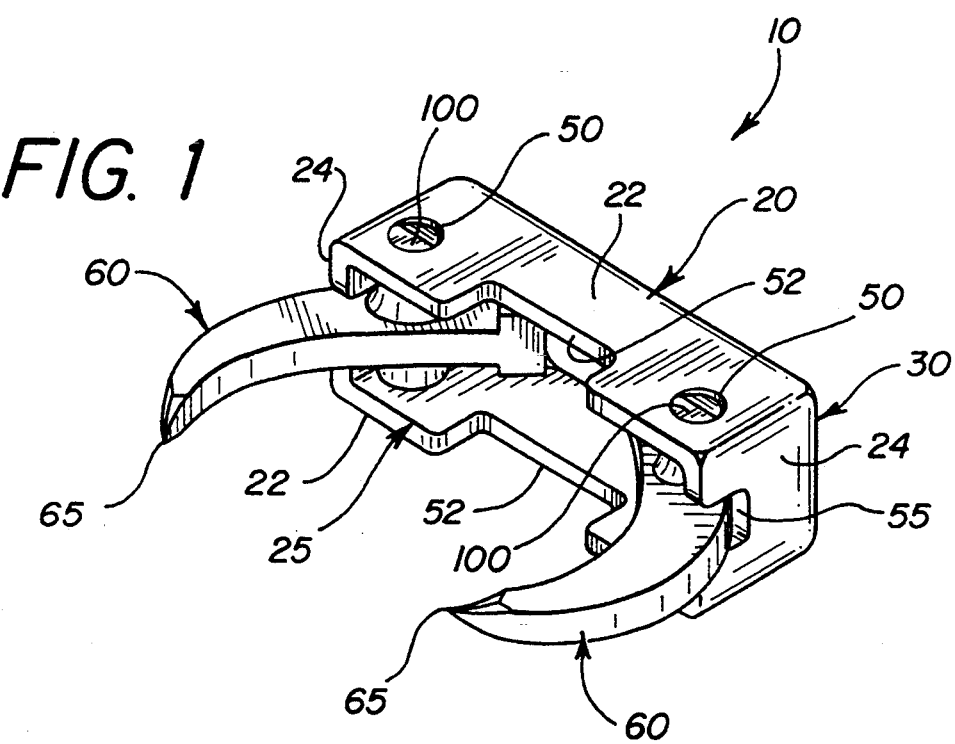
FIG. 1 is a perspective view of a surgical staple of the present invention shown in a first open position as seen from the front.
Figure 2:
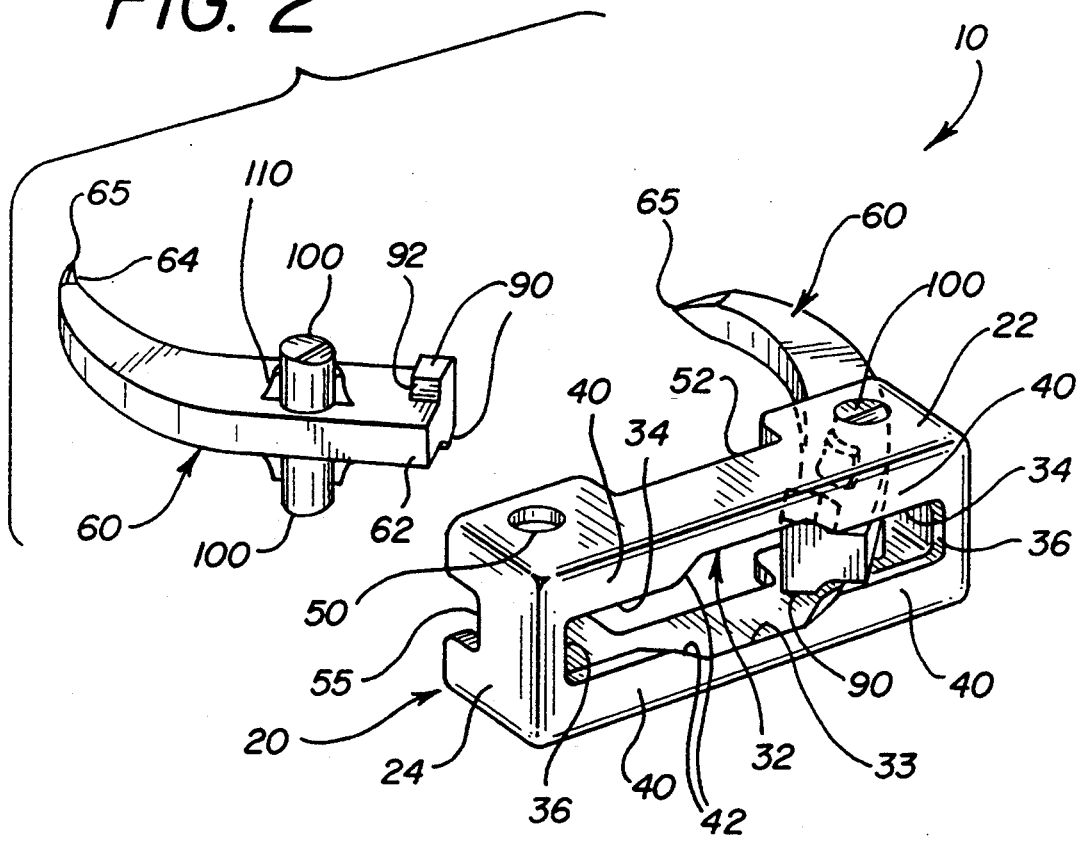
FIG. 2 is a partially exploded perspective view of a surgical staple of the present invention illustrating a leg removed from the crown and also illustrating the top of the crown.
Figure 8:
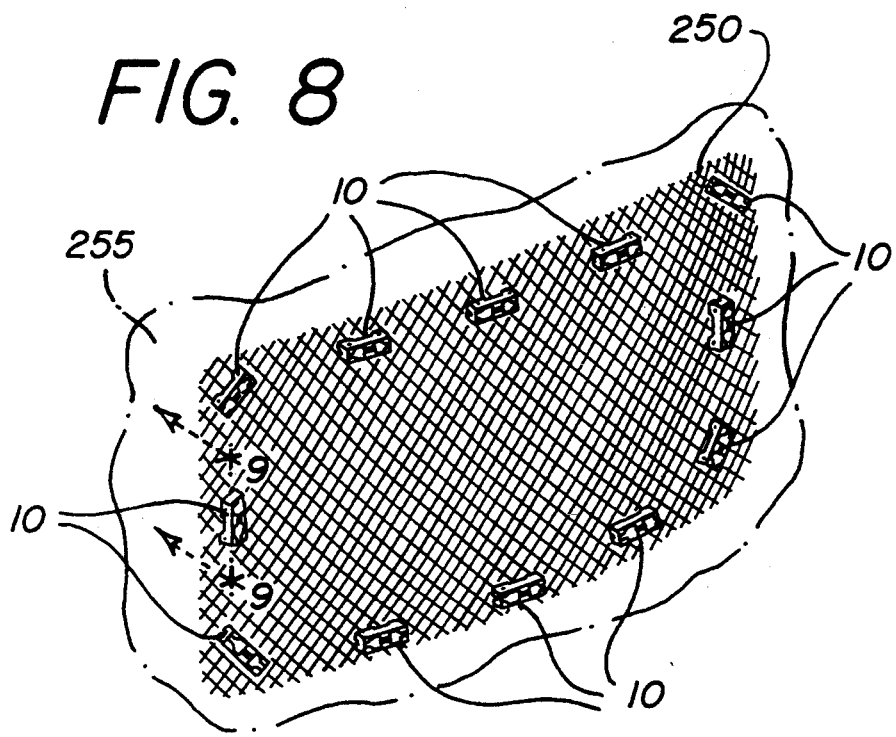
FIG. 8 is a perspective view of surgical staples of the present invention fastening a piece of mesh to a tissue site, wherein the staples have been applied during a surgical procedure.
Figure 9:
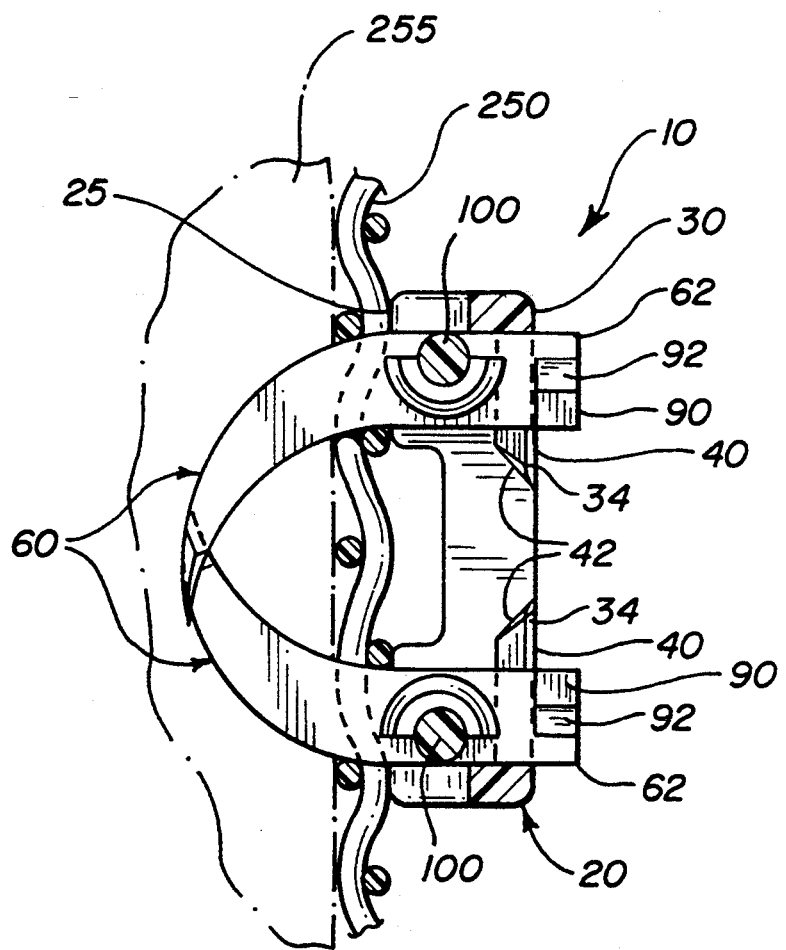
FIG. 9 is a cross-sectional view of a staple as taken along View Line 9—9 of FIG. 8.

As illustrated in FIGS. 1-4 and FIG. 12, the surgical staple 10 of the present invention is seen to have a crown 20 and a pair of curved legs 60. The crown 20 is seen to be a substantially rectangular frame having a pair of opposed longitudinal sides 22 connected to a pair of opposed end sides 24. The crown 20 is seen to have top 30 having slot 32 therein. The crown 20 is seen to have bottom opening 25. The crown 20 is essentially a hollow frame having a passage therethrough from the bottom 25 of the crown 20 up to and through the slot 32 of top 30, although those skilled in the art will appreciate that other frame configurations may be utilized. The slot 32 is seen to have a large central area 33 and narrow end slots 34 extending toward both ends of the crown 20. End slots 34 are each seen to have opening 35 and closed end 36.

On either side of the end slots 34 are the latch flaps 40. Each latch flap 40 is seen to have camming surface 42 adjacent to opening 35 of end slot 34. Each longitudinal side 22 is seen to have pin mounting holes 50 extending therethrough for pivotally mounting the legs 60. The longitudinal sides 22 are also seen to have rectangular notch 52 extending upwardly from the lower edge. The notch 52 allows adjacent staple crowns 20 to be nested upon one another to minimize the space occupied by a stack of staples 10. Each end side 24 is also seen to have clearance slot 55 extending from the lower edge up toward the midpoint of the side 24 for receiving at least part of leg 60.

Referring to FIGS. 5-9, the legs 60 are seen to be elongated members having a proximal end 62 and a distal end 64. Extending from the end of distal end 64 is the piercing tip 65. Piercing tip 65 will be sufficiently sharp and/or pointed to effectively pierce through mammalian tissue. The piercing tip configuration may be modified to accommodate specific tissue types. Piercing tip 65 may have any conventional piercing profile and equivalents thereof. The leg 60 is seen to have an upper section 70 which is substantially straight and a lower curved portion 80. Leg 60 will have sufficient mechanical strength to effectively allow penetration into tissue without undue or catastrophic deflection or buckling. Extending from opposite sides of the proximal end 62 of legs 60 are the locking flaps 90. Also extending from either side of the leg 60 from upper section 70 are the pivot pins 100. Extending about the upper section 70 of leg 60 about the pivot pins 10 are the collars 110 which function to center legs 60 in slot 32. Collars 110 are preferably substantially cylindrical. The locking flaps 90 are seen to each have a camming surface 92. If desired the lower section 80 of the legs 60 may be straight.

Figure 12:
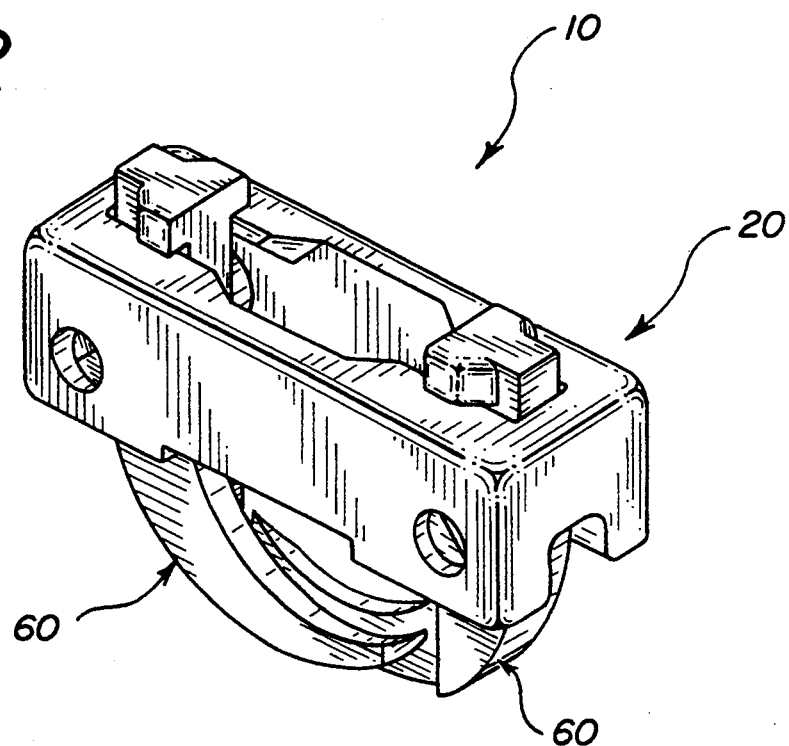
FIG. 12 is a perspective view of a staple of the present invention with the legs in the closed, locked position.

The staples 10 are assembled by inserting the pivot pins 100 into the pivot holes 50 such that a portion of the leg 60 is contained within the slots 55, and the legs are pivotable in pivot holes 50. The proximal ends 62 of legs 60 are prevented from rotating into end slots 34 since the width of each end slot 34 is less than the width of the proximal ends 62. As seen in FIG. 12, when the legs 60 are closed, a section of the legs 60 may overlap. This resulting overlap is due to the relative lengths of the curved portion of the leg 60 and the center to center distance between the crown pivot holes 50.

Figure 10:
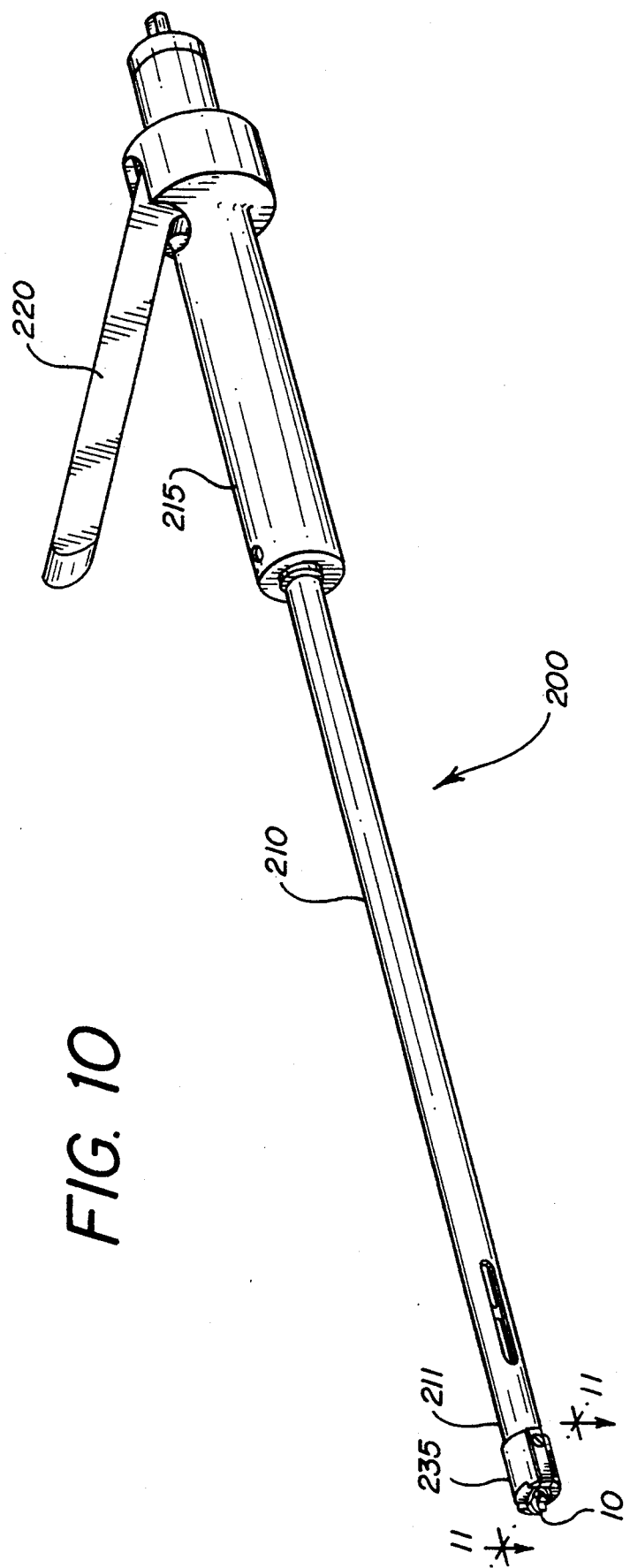
FIG. 10 is a perspective view of a staple applicator surgical instrument used to apply surgical staples of the present invention.
Figure 11:
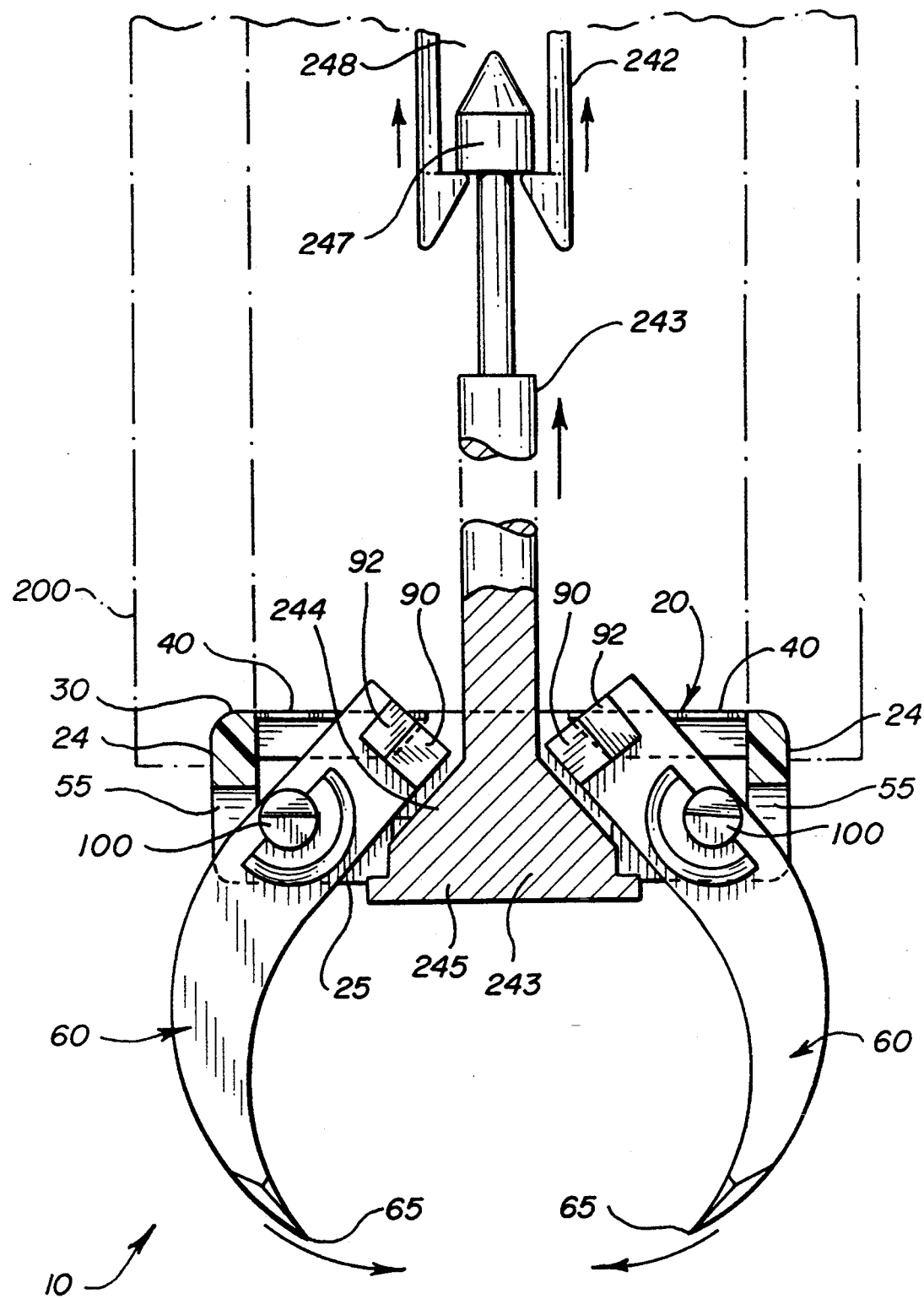
FIG. 11 is a partial cross-sectional view of the staple actuation means of the staple applicator of FIG. 10 as taken along View Line 11—11.
Figure 17:
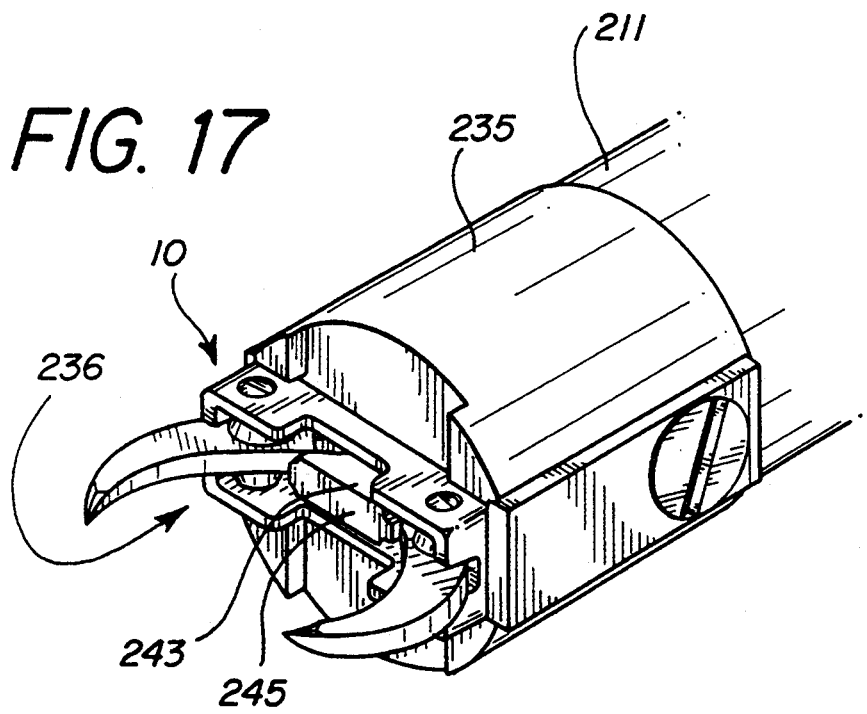
FIG. 17 is a partial perspective view of an applicator having surgical staple contained therein.

An embodiment of an applicator 200 which can be used to apply staples of the present invention such as staple 10 is illustrated in FIGS. 10, 11, and 17. The applicator 200 is see to have tubular frame 210 extending from handle 215. Proximal handle 215 has actuation handle 220 pivotally mounted thereto. Distal end cap 235 is mounted to the distal end 211 of tubular frame 210. Distal end cap 235 is seen to have cavity 236 for receiving at least part of the crown of a staple of the present invention such as crown 20 of staple 10. Actuation rod 240 is slidably mounted within frame 210. Rotation of handle 220 about its pivot point will cause rod 240 to slide within tubular member 210. Proximal end 241 of rod 240 is pivotally mounted to handle 220 while member 243 is seen to extend from the distal end 242. The distal end 242 is seen to have a cavity 248 or equivalent thereof for engaging the proximal end 247 of member 243. Member 243 is seen to have angulated surfaces 244 extending radially and distally outward and flat end section 245. The distal end of member 243 is preferably conically or triangularly shaped. The distal end of member 243 may extend out from the cavity 236 of end cap 235.

Apparatus 200 operates in the following manner. Distal member 243 is released or disengaged from the apparatus 200 where it is gripped by cavity 348 of member 240. A staple 10 is slipped onto the proximal end 247 of member 243 and slid to the distal end until the sloped distal end section of member 243 enters the bottom of the crown 20. The assembly consisting of the staple 10 and member 243 is inserted into the end cap 235 until the proximal end 247 of member 243 is recaptured by cavity 248 in the distal end 242 of rod 240. The staple 10 now fits into the cavity 236 of the end cap 235 which prevents proximal movement of the staple 10. The staple 10 is fired by rotating the handle 220 toward the tubular frame 210 of the applier. Rod 240 is pushed in a linear, proximal direction by virtue of a bushing arrangement on its proximal end and interaction with handle 220. Rod 240 pulls member 243 in a proximal direction. The angular surfaces 244 of member 243 contact the straight portions of the legs 70, causing them to pivot about their pivot pins 100. Member 243 is pulled proximally until it is clear of the staple 10. At this point, the legs 60 are fully rotated and locked. Although not shown, if desired a conventional mechanism for storing and feeding multiple staples 10 may be mounted to applicator 200.

The staples 10 of the present invention operate in the following manner. As seen in FIGS. 8 through 11 and FIG. 17, the staples 10 are grasped by an appropriate surgical grasping instrument or a specially designed applicator 200 and placed into position proximal to the tissue to be stapled. The piercing tips 65 of the legs 60 are positioned substantially perpendicular to the surface of the tissue. The staple 10 is then pushed distally into the tissue such that the distal tips 65 penetrate the tissue up to the bottom surface of crown 20. Then, the proximal ends 62 of each leg 60 are rotated inwardly (one leg will rotate clockwise and one leg will rotate counter-clockwise about the pivot pins 100 such that the proximal ends 62 are forced into the narrow end slots 34 of the slot 32. The rotation is accomplished by distal movement of member 243 of applicator 200 through the crown 20. As the proximal ends 62 are rotated inwardly the camming surfaces 92 of locking flaps 90 engage camming surfaces 42 of latch flaps 40, thereby laterally displacing the latch flaps 40. This may result in the width of the end slots 34 being initially increased until proximal end 62 of leg 60 is contained within slot 34. The locking flaps 90 extending from the proximal ends 62 and the latch flaps 40 on either side of end slots 34 substantially prevent the legs 60 from rotating by effectively locking the proximal ends 62 in the end slots 34.

Figure 13:
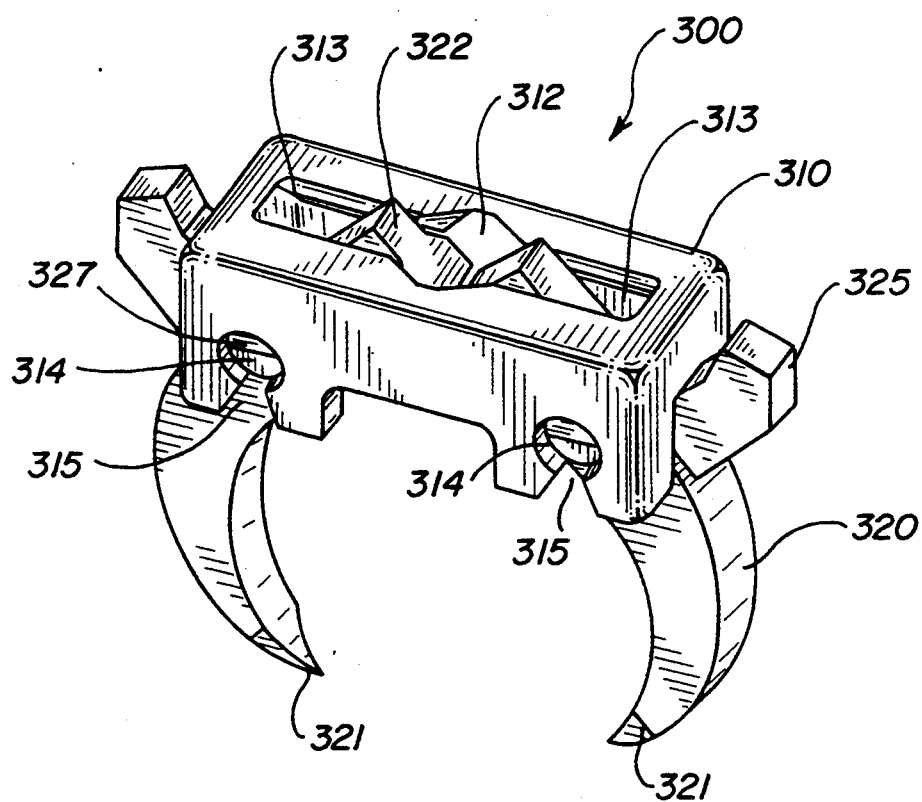
FIG. 13 is a perspective view of an alternative embodiment of a surgical staple of the present invention; actuation levers are seen to be mounted to the legs.

Referring to FIG. 13, staple 300 is seen to be an alternate embodiment of the staples of the present invention. Staple 300 is seen to have frame 310 having slot 312. The frame 310 is seen to have mounting holes 314 having slots 315. The legs 320 are seen to have distal piercing points 321 and proximal ends 322. Extending from each leg 320 is the lever actuation member 325 the legs are seen to have pivot members 327 extending out for mounting in pivot holes 314. The staple is applied by applying a force to lever ends 325 causing the legs 320 to rotate within the pivot holes 314 further causing the proximal end portions 322 of each leg 320 to become locked in the end sections 313 of slot 312. The legs 320 are mounted into the holes 314 by forcing pivot pins 327 in to the slots 315 and causing the frame 310 to elastically deform in the region of the slot 315 and the hole 314 until the pivot member 327 can be located within the hole 314.

Figure 14:
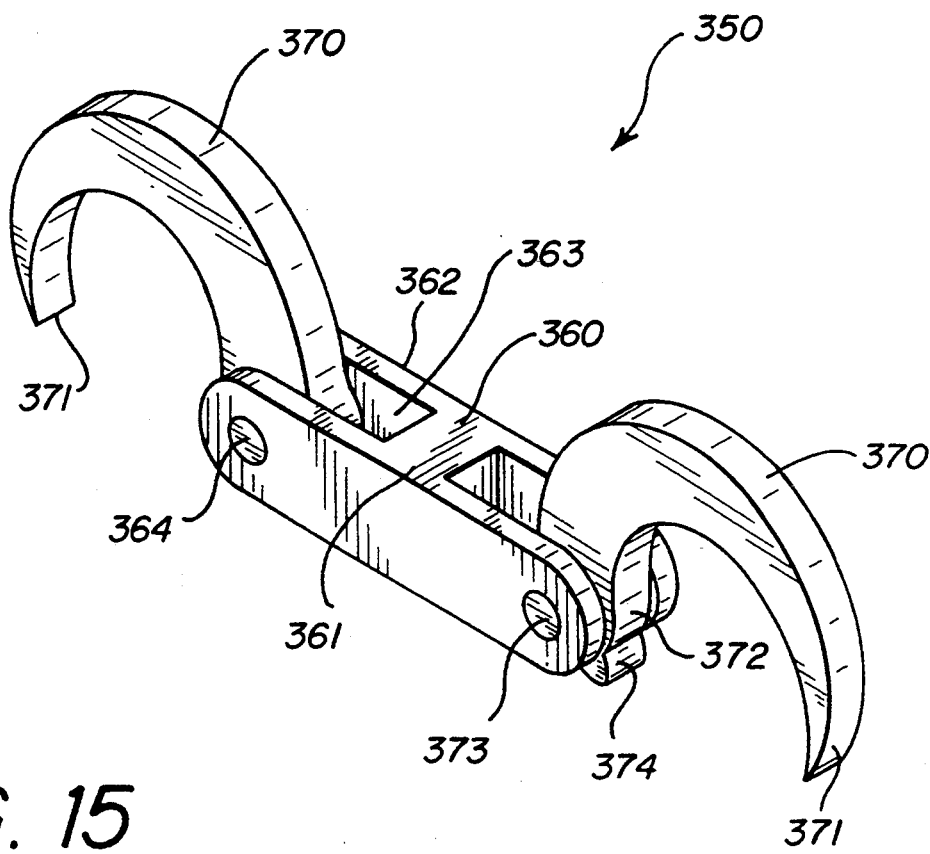
FIG. 14 is yet another embodiment of the surgical staple of the present invention.

Yet another embodiment of the surgical staples of the present invention is seen in FIG. 14. Staple 350 is seen to have frame 360 having central section 361 and outwardly extending yoke members 362. The yoke members 362 are separated by slots 363. The yoke members 362 are seen to have pivot holes 364 at their distal ends. The curved legs 370 are seen to have distal points 371 and proximal ends 372. Extending from ends 372 are the locking members 374. The legs are also seen to have pivot members 373 extending from the distal end. The legs 370 when rotated are locked in place by capturing proximal end 372 in the slots 363.

Figure 15:
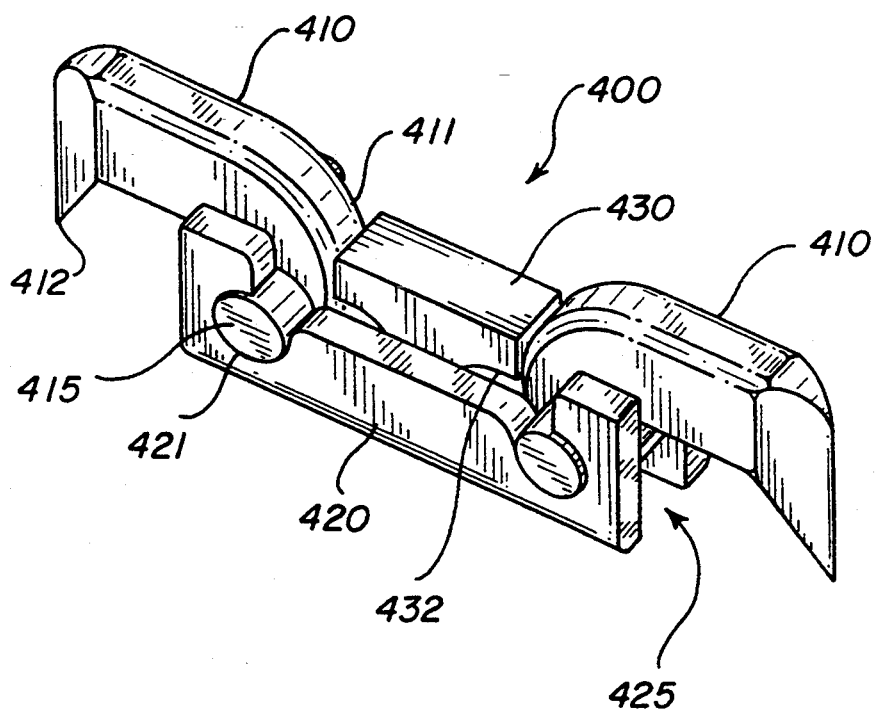
FIG. 15 is a perspective view of yet another embodiment of the present invention.

Surgical staple 400 as seen in FIG. 15 is yet another embodiment of the surgical staples of the present invention. The surgical staple 400 is seen to have leg members 410 which are mounted in frame 420. Frame 420 is seen to have pivot holes 421 for receiving the pivot members 415 and top slots 425. Legs 410 are seen to have proximal ends 411 and distal points 412. Extending from proximal ends 411 are the pivot members 415. As mentioned previously, pivot members 415 extend from proximal ends 411 and are mounted in pivot holes 421. Also, mounted within the slot 425 of the frame 420 is the locking member 430 having ends 432. The locking member 430 is utilized in the following manner to actuate the legs 410. The legs 410 are forced to pivot about the pivot members 415 by an external force. The legs 410 rotate until the proximal portion of each leg cams past locking member 430. The legs 410 will have rotated until their distal points 412 are in the desired extended position and the proximal ends 411 are locked and prevented from rotating further by the member 30.

Figure 16:
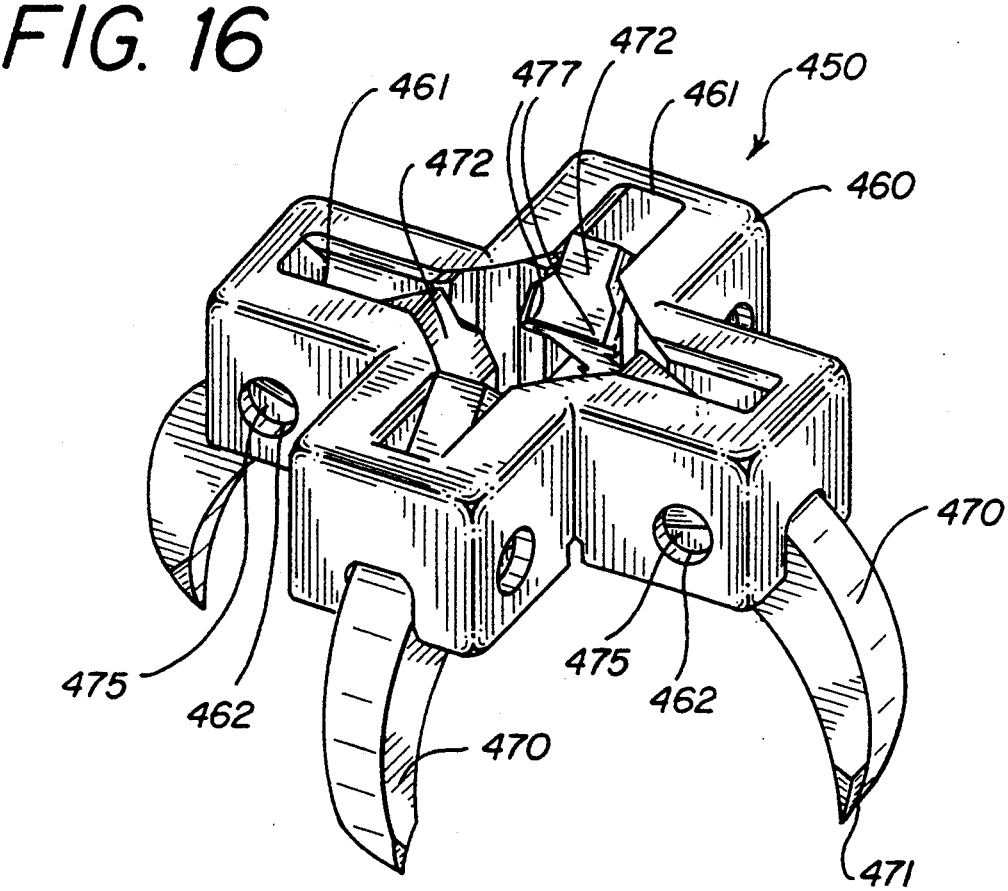
FIG. 16 is a perspective view of the surgical staple of the present invention having multiple movable legs.

The surgical staple 450 as seen in FIG. 16 is yet another embodiment of the surgical staple of the present invention. The surgical staple 450 is seen to have frame 460 having slots 461 and pivot holes 462. Leg members 470 having pivot pins 475 are pivotally mounted in frame member 460. The proximal ends 472 of the leg member 470 are locked into slots 461 after actuation. Leg members 470 have distal points 471. Extending for proximal end 472 of each leg 470 are locking flaps 477. The staples 450 function similarly to staples 10.

Figure 18:
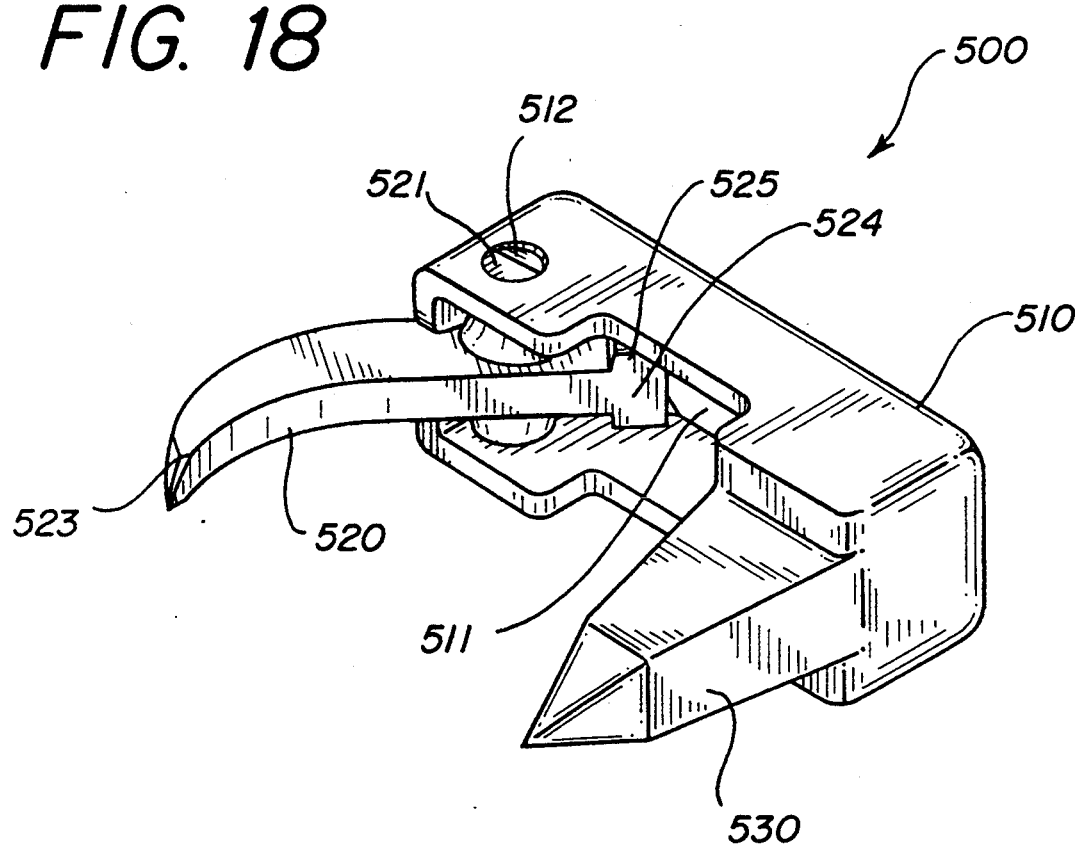
FIG. 18 is a perspective view of a surgical staple of the present invention having one movable leg and one fixed leg.

Another embodiment of the surgical staple present invention is illustrated in FIG. 18. The staple 500 is seen to have frame 510 having slot 511 and pivot mounting holes 512. The leg member 520 has pivot members 521 which are mounted in pivot holes 512. Leg 520 has distal point 523 and proximal end 524 with locking flaps 525. The stationary leg member 530 is seen to extend down from the bottom of the frame 510. Staple 500 is similar in construction and operation to staple 10 except that it has a stationary leg member 530.

The staples 10 of the present invention may be made from either conventional bioabsorbable materials or conventional non-absorbable materials, combinations thereof and equivalents thereof. Examples of absorbable materials include homopolymers and copolymers of lactide, glycolide, trimethylene carbonate, caprolactone, and p-dioxanone and blends thereof. Of particular utility are the following two blends:

(1) the blend of poly(p-dioxanone) and a lactide/-glycolide copolymer, as disclosed in U.S. Pat. No. 4,646,741 which is incorporated by reference.

(2) the glycolide-rich blend of two or more polymers, one polymer being a high lactide content polymer, and the other being a high glycolide content disclosed in U.S. Pat. No.4,889,119 which is incorporated by reference.

The crown 20 and the legs 60 may be made from different materials having different mechanical properties. For example, it may be desirable to have the crown 20 made from an absorbable material having sufficient resiliency to allow the end slots 34 to open, while the legs 60 may be made from an absorbable material having sufficient stiffness to prevent buckling or bending of the legs 60 under mechanical loads.

The staples 10 may also be made from conventional non-absorbable, biocompatible materials including stainless steel, titanium, polymers, composites and the like and equivalents thereof.

The following example is illustrative of the principals of practice of the present invention, although not limited thereto.

EXAMPLE I

A patient is prepared for surgery using conventional surgical preparatory techniques. The patient is anesthetized with a sufficient dose of a conventional anaesthesia to induce an effective anaesthetized state. An incision is made into the patient's abdominal cavity in order to access the site of an inguinal hernia using conventional surgical techniques. After the site of the inguinal hernia is prepared using conventional surgical techniques, a piece of a conventional, biocompatible surgical mesh 250 is placed over the site of the inguinal hernia. Absorbable surgical staples 10 of the present invention are applied by grasping the staples 10 by an appropriate surgical grasping instrument or inserting a staple 10 into a specially designed applicator 200 and placing the staples 10 into position proximal to the tissue to be stapled. The staples 10 are made from a conventional absorbable polymeric material. The piercing tips 65 of the legs 60 are positioned substantially perpendicular to the surface of the tissue 255. The staple 10 is then pushed distally through the mesh 250 into the tissue 255 such that the distal tips 65 penetrate the tissue 255 up to the bottom surface of crown 20. Then, the proximal ends 62 of each leg 60 are rotated inwardly about the pivot pins 100 such that the proximal ends 62 are forced into the narrow end slots 34 of the slot 32 and the legs 60 are locked into position relative to crown 20 (see FIGS. 8 and 9). After the mesh is secured by using a sufficient number of staples 10 to effectively affix the mesh, for example about fifteen, the inguinal hernia procedure is completed in a conventional manner and the incision in the wall of the abdominal cavity is closed using conventional surgical sutures. The surgical staples 10 maintain the surgical mesh over the site of the inguinal hernia and are absorbed by the patient's body over time.

The surgical staples 10 of the present invention have numerous advantages. It is believed that it has not been previously possible to use and insert an absorbable surgical staple from only one side of a mass of tissue. Conventional staplers require access from two or more sides. In addition, the absorbable staples such as staple 10 of the present invention do not require a second lower locking receiver in order to lock the legs 60 in place. Another advantage of the staples 10 of the present is speed of application. In addition, the negative consequences of nerve entrapment may be diminished. Further, the staples 10 of the present invention may eliminate the star-burst effect in x-rays. An additional advantage is that the staples of the present invention may be made small enough to be applied endoscopically.

Although this invention has been shown and described with respect to detailed embodiments thereof, it will be understood by those skilled in the art that various changes in form and detail thereof may be made without departing from the spirit and scope of the claimed invention.

What is claimed is:

1. A surgical staple, comprising:
   a crown comprising a hollow frame having a cavity therein and a passage therethrough;
   mounting means associated with said frame;
   at least two legs, each leg having a distal pointed end and a proximal end, wherein said legs are pivotally mounted to said mounting means; and,
   locking means for locking the legs in a fixed position in the crown.

2. The surgical staple of claim 1 wherein the frame comprises a pair of longitudinal sides and a pair of opposed end sides and a top and a bottom, the top having a slot therein in communication with the cavity of the frame, and the bottom side being open.

3. The surgical staple of claim 2 wherein the locking means comprises a pair of opposed flaps extending from either side of the proximal end of each leg and a pair of flaps extending from each end of the slot.

4. The staple of claim 2 wherein the slot comprises a central section and at least two end sections.

5. The surgical staple of claim 1 wherein the mounting means comprises pivot holes in the frame.

6. The surgical staple of claim 1 wherein the legs comprise outwardly extending pivot posts.

7. The surgical staple of claim 1 wherein the mounting means comprises pivot holes in the legs, 8. The surgical staple of claim 1 wherein the frame additionally comprises pivot posts.

9. The surgical staple of claim 1 wherein the distal end of each leg is curved.

10. The surgical staple of claim 1 wherein the distal end of each leg is substantially straight.

11. The surgical staple of claim 1 further comprising camming means mounted in the crown.

12. The surgical staple of claim 1 further comprising camming means mounted to the proximal end of each leg.

13. The staple of claim 1 wherein the staple comprises absorbable polymers.

14. The staple of claim 1 wherein the staple comprises metal.

15. The staple of claim 1 wherein the staple comprises a non-absorbable polymer, 16. The staple of claim 1 wherein the staple comprises a biocompatible, non-absorbable material.

17. A surgical staple, comprising:
   a crown comprising a hollow frame having a cavity therein and a passage therethrough;
   mounting means associated with said frame;
   at least one pivotable leg, each leg having a distal pointed end and a proximal end, wherein each leg is pivotally mounted to said mounting means;
   at least one fixed leg extending from the crown; and,
   locking means for locking the legs in a fixed position in the crown.

18. The surgical staple of claim 17 wherein the frame comprises a pair of longitudinal sides and a pair of opposed end sides and a top and a bottom, the top having a slot therein in communication with the cavity of the frame, and the bottom side being open.

19. The surgical staple of claim 18 wherein the locking means comprises a pair of opposed flaps extending from either side of the proximal end of each leg and a pair of flaps extending from each end of the slot.

20. The staple of claim 18 wherein the slot comprises a central section and at least one end sections.

21. The surgical staple of claim 17 wherein the mounting means comprises pivot holes in the frame.

22. The surgical staple of claim 17 wherein each pivotable leg comprise outwardly extending pivot posts.

23. The surgical staple of claim 17 wherein the mounting means comprises pivot holes in each legs.

24. The surgical staple of claim 17 wherein the frame additionally comprises pivot posts.

25. The surgical staple of claim 17 wherein the distal end of each pivotable leg is curved.

26. The surgical staple of claim 17 wherein the distal end is substantially straight.

27. The surgical staple of claim 17 further comprising camming means mounted in the crown.

28. The surgical staple of claim 17 further comprising camming means mounted to the proximal end of each pivotable leg.

29. A method of applying a surgical staple in a surgical procedure, wherein the staple comprises a crown comprising a hollow frame having a cavity therein and a passage therethrough and at least one leg member pivotally mounted to the crown, the method comprising:

inserting the legs of the surgical staple through one side of a section of tissue; and, rotating and locking each pivotally-mounted leg to secure the staple to the section of tissue.

30. A device for applying a surgical staple wherein the staple comprises a crown comprising a hollow frame having a cavity therein and a passage therethrough and at least two pivotally mounted legs mounted to the frame, the device comprising:

a tubular frame having a proximal end and a distal end;

a handle mounted to the proximal end;

an actuation rod slidably mounted in the tubular frame, said rod having a distal end and a proximal end; an actuation means mounted to the handle for engaging the proximal end of the actuation rod;

means for holding the staple mounted to the distal end of the tubular frame; and, means for engaging the legs of the staple in response to proximal movement of the rod, said means mounted to the distal end of the rod.

31. The device of claim 30 wherein the leg engaging means comprises a conically shaped member.

32. The device of claim 30 wherein the leg engaging means comprises a triangularly shaped member.

33. The device of claim 30 wherein the device further comprises means for disengaging the leg engaging means from the distal end of the rod.

* * * * *